United States Patent [19]

Simon

[11] Patent Number: 4,727,087

[45] Date of Patent: * Feb. 23, 1988

[54] PHARMACEUTICAL COMPOSITION AND METHOD OF TREATMENT

[76] Inventor: Hector C. Simon, Orizaba, Veracruz, Mexico

[*] Notice: The portion of the term of this patent subsequent to Apr. 24, 2001 has been disclaimed.

[21] Appl. No.: 744,647

[22] Filed: Jun. 13, 1985

Related U.S. Application Data

[63] Continuation of Ser. No. 534,398, Sep. 23, 1983, abandoned, which is a continuation of Ser. No. 380,884, May 21, 1982, abandoned, which is a continuation of Ser. No. 195,080, Oct. 8, 1980, abandoned, which is a continuation of Ser. No. 64,587, Aug. 7, 1979, abandoned, which is a continuation of Ser. No. 852,960, Nov. 18, 1977, abandoned, which is a continuation of Ser. No. 700,150, Jun. 28, 1976, abandoned, which is a continuation-in-part of Ser. No. 521,410, Nov. 6, 1974, abandoned.

[30] Foreign Application Priority Data

Aug. 8, 1974 [MX] Mexico ................................ 153061

[51] Int. Cl.$^4$ ............................................. A61K 31/12
[52] U.S. Cl. ..................................................... 514/691
[58] Field of Search ......................................... 514/691

[56] References Cited

PUBLICATIONS

Leiter et al, Cawler Research, Part 2, vol. 25, No. 5, Jun., 1965, pp. 1077–1085, 1091 and 1125, (No. 62612).
Carter et al, Chemotherapy of Cawler, 2nd ed., John Wiley & Sons, N.Y., N.Y., 1981, pp. 26–43.

*Primary Examiner*—Jerome D. Goldberg
*Attorney, Agent, or Firm*—Hopgood, Calimafde, Kalil, Blaustein & Judlowe

[57] ABSTRACT

A pharmaceutical composition and method of treatment is provided for aiding the regression and palliation of cancers selected from the group consisting of leukemia, Ewing's sarcoma, stomach diffuse carcinoma, vesical adeno-carcinoma, lymphosarcoma, uterine cancer and lung cancer in humans which comprises the administration of a therepeutically effective amount of the said composition comprising friendelan-3-one contained in a physiologically acceptable solution.

5 Claims, No Drawings

PHARMACEUTICAL COMPOSITION AND METHOD OF TREATMENT

This application is a continuation of application Ser. No. 534,398, filed Sept. 23, 1983, now abandoned, which is a continuation of application Ser. No. 380,884, filed May 21, 1982, now abandoned, which is a continuation of application Ser. No. 195,080, filed Oct. 8, 1980, now abandoned, which is a continuation of application Ser. No. 064,587, filed Aug. 7, 1979, now abandoned, which is a continuation of application Ser. No.852,960, filed Nov. 18, 1977, now abandoned, which is a continuation of application Ser. No. 700,150, filed June 28, 1976, now abandoned, which is a continuation-in-part of application Ser. No. 521,410, filed Nov. 6, 1974, now abandoned.

This invention relates to a pharmaceutical composition for the treatment of various forms of cancer and to a method of treatment which aids in the regression and palliation of cancerous growth in humans.

BACKGROUND OF THE INVENTION

Cancer is generally defined as an abnormal and unrestrained new growth in cells and tissues that produces adverse effects in man and which is often fatal. Thus, when for no understandable reason, cells and tissues grow more rapidly than normal and develop abnormal shapes and sizes and cease functioning in a normal manner, they are said to be malignant or cancerous.

Cancers can be divided into three broad groups: carcinomas, sarcomas and leukemias or lymphomas. Carcinomas arise in the epithelia, the sheets of cells covering the surface of the body and the lining of various glands. Sarcomas generally arise in the supporting tissues such as fibrous tissues and blood vessels and leukemias or lymphomas arise in the blood-forming cells of the bone marrow and the lymph nodes. Carcinomas are the most prevalent, while sarcomas and leukemia are less so. These cancers can be further classified by the organs in which they originate or by the types of cell involved. Considered in this way, there are 100 or so distinct varieties of the disease. Roughly half of all cancer deaths are caused by cancer of three organs: the lung, the large intestine and the breast.

Many types of cancers are capable of being diagnosed. For example, at least 50% of all cancers are visible upon inspection and at least 25% more can be detected with special examining instruments capable of being inserted within body orifices. Many cancers have recognizable symptoms. Urinary cancer, for example, produces an initial symptom of hematuria, i.e. blood in the urine, the disease being usually accompanied by frequent urination and pain. The location of the cancer can be determined by X-ray and cystoscopic visualization of the urinary bladder itself and its treatment can therefore be monitored. Cancer of the lung has been increasing in frequency in the past 10 or 15 years. It is usually accompanied by the onset of a persistent cough which may not appear serious at the time until blood appears in the phlegm. Various other forms of cancer can be debilitating and may be accompanied by loss of appetite, loss of weight, changes in disposition, changes in skin tone, and other noticeable symptoms.

While it is appreciated that the field of cancer therapy has been the subject of intensive research and study in recent years in which a large phase of the study has been directed to chemotherapy, very few effective substances have been found for alleviating the condition and, so far as is known, there is no effective general cure. For many cancers, there is no specific drug, the treatment employed being whatever combination of surgery, radiation and cytotoxic drugs (chemotherapy) which have been found empirically to give the best results.

I have now discovered a pharmaceutical composition which is effective in aiding the regression and palliation of cancers selected from the group consisting of leukemia, Ewing's sarcoma, stomach diffuse carcinoma, vesical adeno-carcinoma, lymphosarcoma, uterine cancer and lung cancer in humans in humans and a method of treatment by which regular administration of minute amounts of the composition provide noticeable physiological improvement in the cancer-bearing human.

STATE OF THE ART

Tests on friedelan-3-one (also known as friedoolean-3-one) are reported together with other drugs in *Cancer Research Supplement*, Vol. 25, No. 5, June 1965 in a paper entitled "Cancer Chemotherapy Screening Data XXXVII", pp 1077 et seq., in particular page 1125. The compound was tested dissolved in carboxymethylcellulose and was administered into mice by injection (intraperitoneal). According to the paper, the data were reported only on compounds which did not demonstrate sufficient activity in cancer systems tested to warrant further investigation. Nevertheless, the same compound was found, in accordance with the present invention, to be beneficially active when administered orally in a physiologically acceptable solution to humans in therapeutically effective amounts.

OBJECTS OF THE INVENTION

It is thus an object of the invention to provide a pharmaceutical composition for use in inhibiting the growth of cancerous cells in cancers selected from the group consisting of leukemia, Ewing's sarcoma, stomach diffuse carcinoma, vesical adeno-carcinoma, lymphosarcoma, uterine cancer and lung cancer in humans and alleviating the symptoms attendant thereto.

Another object of the invention is to provide a method for aiding in the regression and palliation of cancers selected from the group consisting of leukemia, Ewing's sarcoma, stomach diffuse carcinoma, vesical adeno-carcinoma, lymphosarcoma, uterine cancer and lung cancer in humans in man by the administration of said pharmaceutical composition contained in a physiologically acceptable solution.

These and other objects of the invention will more clearly appear when taken in conjunction with the following disclosure and the accompanying claims.

STATEMENT OF THE INVENTION

Stating it broadly, my invention resides in a pharmaceutical composition for inhibiting the growth of cancer in humans comprising a small but therapeutically effective amount of friedelan-3-one dissolved in a pharmaceutically acceptable solution . (The compound "friedelan-3-one" is also known in the literature as "friedooleanan-3-one"). When I use the term "friedelan-3-one", I also mean to include the derivatives thereof having similar properties.

Preferably, the solution comprises dissolving said small but effective amount of friedelan-3-one in ethanol in amounts ranging by weight from about 0.01% to 0.4% by weight of solution. This solution is used as a master solution from which doses are produced by adding a predetermined amount of said solution to a sufficient amount of a pharmaceutically or physiologically acceptable carrier, such as water or other beverage, to enable the oral consumption of said diluted composition by a patient under treatment. The term "beverage" herein is meant to include water, fruit juices or other orally consumable liquid.

The dosage amounts may range preferably from about one to about fifteen drops (or even up to about 50 drops) of the aforementioned solution added to a beverage (e.g. water) to be taken by a patient at least before each meal on a daily basis under the supervision of a physician. The preferred master composition is one containing approximately 0.04% friedelan-3-one dissolved in ethanol. At this concentration, the master solution contains about 6.5 micrograms ($\mu$g) of the active ingredient per drop. The size of the foregoing drops using a No. 20 dropper is such that approximately 50 drops equals one millimeter (ml) of solution.

The foregoing drug may further contain pharmaceutical adjuvants, for example, chlorophyll and a phenolic resin, e.g. phenolformaldehyde. Thus, the pharmaceutical composition may comprise by weight about 0.01% to 0.4% of friedelan-3-one, about 0.006% to 0.12% chlorophyll and about 0.6% to 3.7% of said phenolic resin dissolved in ethanol, a specific composition containing about 0.04% friedelan-3-one, about 0.2% chlorophyll and 1.65% phenolic resin. The latter composition is obtained by dissolving 0.033 gr friedelan-3-one, 0.166 gr chlorophyl and 1.3326 gr phenolic resin in 100 ml of ethanol. It appears that the adjuvants aid in counteracting odors typical of certain cancers. Whatever their action, I have found these adjuvants to be quite useful when combined with the solution containing friedelan-3-one.

While the doses suggested are very dilute, a slight side effect may occur when the foregoing composition is orally administered to a patient. Such side effects may be accompanied by a gradual rise in temperature accompanied by a slight headache and mild pains in certain joints and are not serious. Such headaches and/or pains can be treated with aspirin or other well known pain-relieving drugs.

A 0.04% solution of friedelan-3-one is obtained by dissolving about 0.003 gr of the compound in ethanol which has a density of about 0.79 grs/ml, 100 ml of ethanol weighing about 79 grams. About 6 to 7 micrograms ($\mu$g) of friedelan-3-one is contained in a drop of a 0.04% solution. While ethanol is preferred as the carrier, other pharmaceutically acceptable solvents for oral consumption by a patient may be employed.

The compositions of the invention is used under a physician's direction in prescribed dosage amounts which may preferably vary from about 1 to 15 drops (or up to 50 drops), with each dose containing an amount of friedelan-3-one ranging from about 2 to 60 $\mu$g, and generally from about 6 to 15 $\mu$g.

As a general guideline, one drop of master solution per 10 kg of body weight is an acceptable dosage amount.

Observations of patients by a physician have indicated that the drug is not considered toxic when taken orally in dosage amounts of several or more drops of a 0.04% ethanol solution diluted in one, two or more ounces of water or other beverage, e.g. fruit juices.

Dosage amounts of up to 5 or more drops of a 0.04% ethanol solution diluted in a beverage taken several times a day over a period of time of several or more months have indicated the drug to be therapeutically active in patients treated for Ewings Sarcoma of the hip, Stomach Diffuse Carcinoma (Plastic Linitis) and Vesical Adeno-Carcinoma well differentiated. In the case of Ewing's Sarcoma, three drops (18 to 19 $\mu$g) of 0.04%, solution in water was prescribed three times daily for about 7 months. In the case of Stomach Diffuse Carcinoma, a dose of 4 to 8 drops (26 to 52 $\mu$g) in water was prescribed and taken orally 3 to 7 times a day for over a year.

Therapeutic activity of the composition of the invention was also indicated in the treatment of other patients suffering from various forms of leukemia, lymphosarcoma, uterine cancer, cancer of the lung, etc.

An ethanol solution containing 0.04% by weight of friedelan-3-one was employed, one drop of solution (about 6 to 7 $\mu$g of friedelan-3-one) being used for each 10 kg of body weight taken 3 to 7 times a day, depending on the gravity of the illness. This corresponds to a daily dose rate per 10 kg of body weight of approximately 20 to 46 $\mu$g. The patients were treated from 2 to 22 months. In a number of cases, other methods of conventional therapy were used in conjunction with the pharmaceutical composition of the invention.

Of twenty patients studied, fourteen responded beneficially to the treatment. Four exhibited regular results, while in two instances, there was no noticeable therapeutic activity. No serious side effects were observed.

As will be apparent from the foregoing studies, the composition of the invention is efficacious in the treatment of cancer-bearing humans by use of small but effective does. As stated earlier, tests to date have not indicated any substantial degree of harmful toxicity with said composition.

Thus, by working over the composition ranges set forth hereinabove, dosage amounts can be prescribed compatible with the system of the cancer-bearing patient. The small but effective dosage amounts when prescribed for a patient may range from a drop of the master solution to upwards of about 15 drops or more added to an orally consumable amount of beverage, the amount of drug being determined by an attending physician familiar with the case. It is preferred that, in diluting the ethanol composition in water for oral use, the final ethanol content of the solution not exceed 5% by weight and preferably be below 2% or below 1%. Generally, the younger the patient, the lower the dosage amount over the range stated hereinabove, the preferred 1 to 15 drops of the master solution in water being administered orally at least once a day, and preferably at least once before each meal on a daily basis, until a determination has been made that the patient's condition has improved and the symptoms of cancerous growth palliated.

Although the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the invention and the appended claims.

What I claim is:

1. A method of aiding the regression and palliation of cancer selected from the group consisting of leukemia, Ewing's sarcoma, stomach diffuse carcinoma, vesical adeno-carcinoma, lymphosarcoma, uterine cancer and lung cancer in humans which comprises administering orally to an affected human a physiologically acceptable solution containing an amount of friedelan-3-one therapeutically effective to aid in the regression and palliation of said cancer.

2. A method for aiding the regression and palliation of cancer selected from the group consisting of leukemia, Ewing's sarcoma, stomach diffuse carcinoma, vesical adeno-carcinoma, lymphosarcoma, uterine cancer and lung cancer in humans which comprises administering orally to an affected human a solution containing about 0.01% to 0.4% by weight of friedelan-3-one dissolved in ethanol, said solution being administered at regular intervals on a daily basis in dosage amounts diluted in a beverage to enable the oral ingestion of said solution therapeutically effective to aid in the regression and palliation of said cancer.

3. The method of claim 2, wherein said ethanol solution contains approximately 0.04% by weight of freidelan-3-one.

4. A method for aiding the regression and palliation of cancer selected from the group consisting of leukemia, Ewing's sarcoma, stomach diffuse carcinoma, vesical adeno-carcinoma, lymphosarcoma, uterine cancer and lung cancer in humans which comprises orally administering to an affected human a solution containing about 0.01% to 0.4% by weight of friedelan-3-one dissolved in ethanol, said solution being administered at regular intervals on a daily basis in dosage amounts corresponding to about 2 to 60 μg of friedelan-3-one diluted in a beverage to enable the oral ingestion of said solution.

5. The method of claim 4, wherein said ethanol solution contains approximately 0.04% by weight of friedelan-3-one.

* * * * *